US00PP33466P2

(12) United States Plant Patent
van Sambeek

(10) Patent No.: US PP33,466 P2
(45) Date of Patent: Sep. 7, 2021

(54) ***GERANIUM* PLANT NAMED 'DOGERGARGEMAM'**

(50) Latin Name: ***Geranium sanguineum* X *Geranium himalayense***
Varietal Denomination: Dogergargemam

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/084,503

(22) Filed: Oct. 29, 2020

(51) Int. Cl.
*A01H 5/02* (2018.01)
*A01H 6/42* (2018.01)

(52) U.S. Cl.
USPC ..... Plt./324
CPC ..... *A01H 6/42* (2018.05)

(58) Field of Classification Search
USPC ..... Plt./324
CPC ..... A01H 6/42
See application file for complete search history.

(56) References Cited

PUBLICATIONS

UPOV hit on a *Geranium* hybrid plant named 'Dogergargemam', QZ PBR 2019/2745, published Oct. 30, 2019.*

* cited by examiner

*Primary Examiner* — Anne Marie Grunberg
(74) *Attorney, Agent, or Firm* — C. Anne Whealy

(57) ABSTRACT

A new and distinct cultivar of *Geranium* plant named 'Dogergargemam', characterized by its low-growing and outwardly spreading plant habit; vigorous growth habit; freely branching habit; freely flowering habit; upward-facing purple violet-colored flowers with glossy dark purple-colored venation and small white-colored centers; long and continuous flowering period; and good garden performance.

2 Drawing Sheets

Botanical designation: *Geranium sanguineum* X *Geranium himalayense.*
Cultivar denomination: 'Dogergargemam'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Oct. 30, 2019, application number 2019/2745. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Geranium* plant, botanically known as *Geranium sanguineum* X *Geranium himalayense* and hereinafter referred to by the name 'Dogergargemam'.

The new *Geranium* plant is a product of a planned breeding program conducted by the Inventor in Aalsmeer, The Netherlands. The objective of the breeding program is to create new *Geranium* plants with numerous attractive flowers.

The new *Geranium* plant originated from a cross-pollination made by the Inventor in June, 2015 in Aalsmeer, The Netherlands of *Geranium sanguineum* 'Striatum', not patented, as the female, or seed, parent with *Geranium himalayense* 'Johnson's Blue', not patented, as the male, or pollen, parent. The new *Geranium* plant was discovered and selected by the Inventors as a single flowering plant within the progeny of the stated cross-pollination in a controlled environment in Aalsmeer, The Netherlands in June, 2016.

Asexual reproduction of the new *Geranium* plant by terminal cuttings in a controlled environment in Aalsmeer, The Netherlands since March, 2017, has shown that the unique features of this new *Geranium* plant are stable and reproduced true to type in successive generations.

SUMMARY OF THE INVENTION

Plants of the new *Geranium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dogergargemam'. These characteristics in combination distinguish 'Dogergargemam' as a new and distinct *Geranium* plant:

1. Low-growing and outwardly spreading plant habit.
2. Vigorous growth habit.
3. Freely branching habit.
4. Freely flowering habit.
5. Upward-facing purple violet-colored flowers with glossy dark purple-colored venation and small white-colored centers.
6. Long and continuous flowering period.
7. Good garden performance.

Plants of the new *Geranium* differ primarily from plants of the female parent, 'Striatum' in flower color as plants of the new *Geranium* have purple violet-colored flowers with glossy dark purple-colored venation whereas flowers of plants of 'Striatum' are light pink in color with darker pink-colored venation.

Plants of the new *Geranium* differ primarily from plants of the male parent, 'Johnson's Blue' in flower color as plants of the new *Geranium* have purple violet-colored flowers with glossy dark purple-colored venation whereas flowers of plants of 'Johnson's Blue' are light blue in color with pink-colored venation.

Plants of the new *Geranium* can be compared to plants of *Geranium sanguineum* 'Max Frei', not patented. In side-by-side comparisons, plants of the new *Geranium* differ primarily from plants of 'Max Frei' in flower color as plants of the new *Geranium* have purple violet-colored flowers with glossy dark purple-colored venation whereas flowers of plants of 'Max Frei' are pink in color with darker pink-colored venation.

Plants of the new *Geranium* can also be compared to plants of *Geranium himalayense* 'Gravetye', not patented. In side-by-side comparisons, plants of the new *Geranium* differ primarily from plants of 'Gravetye' in flower color as plants of the new Geranium have purple violet-colored flowers with glossy dark purple-colored venation whereas flowers of plants of 'Gravetye' are blue in color with purple-colored venation.

BRIEF DESCRIPTION OF THE PHOTOGRAPHS

The accompanying colored photographs illustrate the overall appearance of the new *Geranium* plant showing the colors as true as it is reasonably possible to obtain in colored reproductions of this type. Colors in the photographs may differ slightly from the color values cited in the detailed botanical description which accurately describe the colors of the new *Geranium* plant.

The photograph on the first sheet comprises a top perspective view of typical flowering plants of 'Dogergargemam' grown in an outdoor nursery.

The photograph on the second sheet is a close-up view of a typical flower of 'Dogergargemam' (top of sheet) and a typical leaf of 'Dogergargemam' (bottom of sheet).

DETAILED BOTANICAL DESCRIPTION

The aforementioned photographs and following observations, measurements and values describe plants grown during the summer and autumn in ground beds in an outdoor nursery in De Kwakel, The Netherlands. During the production of the plants, temperatures ranged from 11.4° C. to 20.6° C. and light levels averaged 1621.686 J/cm$^2$. Plants were 24 weeks old when the photographs and the description were taken. In the detailed description, color references are made to The Royal Horticultural Society Colour Chart, Second Edition, except where general terms of ordinary dictionary significance are used.

Botanical classification: *Geranium sanguineum* X *Geranium himalayense* 'Dogergargemam'.

Parentage:

*Female, or seed, parent.*—*Geranium sanguineum* 'Striatum', not patented.

*Male, or pollen, parent.*—*Geranium himalayense* 'Johnson's Blue', not patented.

Propagation:

*Type.*—By terminal cuttings.

*Time to initiate roots, summer.*—About seven days at temperatures about 26° C.

*Time to initiate roots, winter.*—About ten days at temperatures about 23° C.

*Time to produce a rooted young plant, summer.*—About 18 days at temperatures about 23° C.

*Time to produce a rooted young plant, winter.*—About 21 days at temperatures about 18° C.

*Root description.*—Thick, fibrous; typically white in color, actual color of the roots is dependent on substrate composition, water quality, fertilizer type and formulation, substrate temperature and physiological age of roots.

*Rooting habit.*—Moderate branching; medium density.

Plant description:

*Plant and growth habit.*—Hardy herbaceous perennial; low-growing and outwardly spreading plant habit; vigorous growth habit and rapid growth rate.

*Plant height.*—About 32 cm.

*Plant width.*—About 100 cm.

*Branching habit.*—Freely branching habit with about five primary branches with lateral branches potentially developing at every node.

*Lateral branch length.*—About 50 cm.

*Lateral branch diameter.*—About 5 mm.

*Internode length.*—About 9 cm.

*Lateral branch aspect.*—Outwardly and horizontally spreading; creeping.

*Lateral branch strength.*—Strong.

*Lateral branch texture and luster.*—Pubescent; semi-glossy.

*Lateral branch color, developing.*—Close to 145A; at the internodes, close to 51A.

*Lateral branch color, developed.*—Close to 143B; at the internodes, close to 51A.

Leaf description:

*Arrangement.*—Opposite, simple.

*Length.*—About 9 cm.

*Width.*—About 11 cm.

*Shape.*—Deeply dissected; palmatifid.

*Apex.*—Mucronate.

*Base.*—Sagittate.

*Margin.*—Palmately lobed; ciliate; sinuses divergent.

*Venation pattern.*—Palmate; reticulate.

*Texture, upper and lower surfaces.*—Pubescent; rough; matte.

*Color.*—Developing leaves, upper surface: Close to 144C. Developing leaves, lower surface: Close to 144A. Fully developed leaves, upper surface: Close to 137A; venation, close to 144A. Fully developed leaves, lower surface: Close to 137C; venation, close to 137D.

*Petioles.*—Length: About 3 cm. Diameter: About 2 mm. Strength: Moderately strong. Texture and luster, upper and lower surfaces: Pubescent; semi-glossy.

Color, upper surface: Close to 144A tinged with close to 51A. Color, lower surface: Close to 144B.

Flower description:

*Flowering habit*.—Single rotate flowers; flowers axillary; flowers face mostly upright; freely flowering habit with about 90 flowers and flower buds developing per plant.

*Fragrance*.—None detected.

*Flowering season*.—In The Netherlands, flowering is continuous from June to October; plants begin flowering about 16 weeks after planting.

*Flower longevity*.—Individual flowers last about seven to ten days on the plant; flowers not persistent.

*Flower buds*.—Length: About 1.4 cm. Diameter: About 1 cm. Shape: Elliptical. Texture and luster: Pubescent; matte. Color: Petals, close to 80A and sepals, close to 143A.

*Flower diameter*.—About 4.5 cm.

*Flower height* (*depth*).—About 1.5 cm.

*Petals*.—Quantity per flower: Five in a single whorl; imbricate. Length: About 2 cm. Width: About 2.2 cm. Shape: Obovate. Apex: Truncate. Base: Obtuse. Margin: Denticulate; slightly undulate. Texture and luster, upper and lower surfaces: Smooth, glabrous; matte; venation is glossy. Color: When opening, upper and lower surfaces: Close to 80A. Fully opened, upper surface: Close to 80A; towards the base, close to 155D; venation, close to 79A; with subsequent development, main color becoming closer to 80A with random patches, close to 88A. Fully opened, lower surface: Close to 81A; venation, close to 77A; with subsequent development, main color becoming closer to 80A.

*Sepals*.—Quantity per flower: Five, arranged in a single whorl. Length: About 1 cm. Diameter: About 5 mm. Shape: Elliptical. Apex: Cuspidate. Base: Cordate. Margin: Entire. Texture and luster, upper surface: Smooth, glabrous; glossy. Texture and luster, lower surface: Pubescent; semi-glossy. Color: When opening and fully opened, upper surface: Close to 144A. When opening and fully opened, lower surface: Close to 143A.

*Peduncles*.—Length: About 4.5 cm to 8.5 cm. Diameter: About 1 mm. Aspect: About 45° from lateral branch. Strength: Weak, flexible. Texture and luster: Pubescent; semi-glossy. Color: Close to 143B tinged with close to 51A.

*Reproductive organs*.—Androecium: Stamen quantity per flower: About ten. Filament length: About 6 mm. Filament color: Close to 78A. Anther size: About 1 mm by 0.5 mm. Anther shape: Oblong. Anther color: Close to 78A. Pollen amount: None observed. Gynoecium: Pistil quantity per flower: One. Pistil length: About 9 mm. Stigma diameter: About 2 mm. Stigma shape: Five-parted. Stigma color: Close to 77A. Style length: About 2 mm. Style color: Close to 187B. Ovary color: Close to 144D and pubescence, close to 155D.

*Seeds and fruits*.—To date, seed and fruit development have not been observed on plants of the new *Geranium*.

Pathogen & pest resistance: To date, plants of the new *Geranium* have been not been observed to be resistant to pathogens and pests common to *Geranium* plants.

Garden performance: Plants of the new *Geranium* have been observed to have good garden performance; to tolerate rain, wind and temperatures ranging from −30° C. to 40° C.

It is claimed:

1. A new and distinct *Geranium* plant named 'Dogergargemam' as illustrated and described.

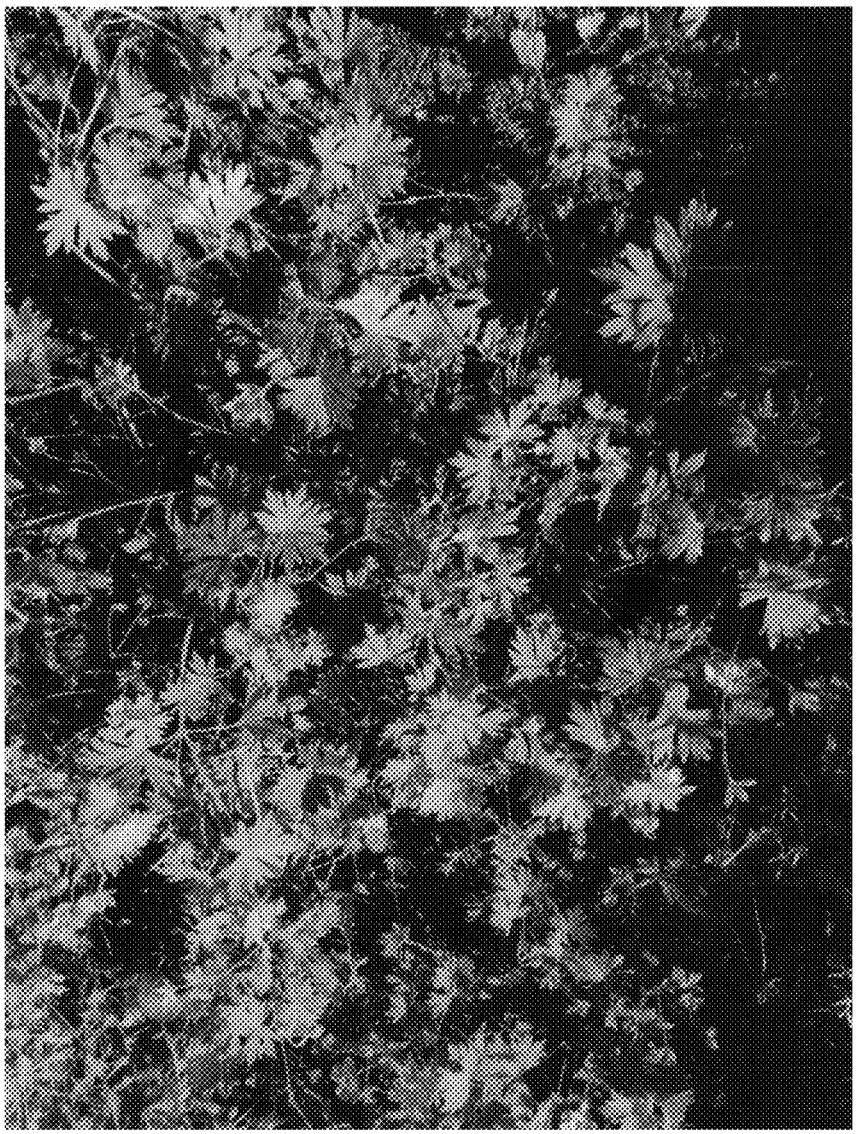

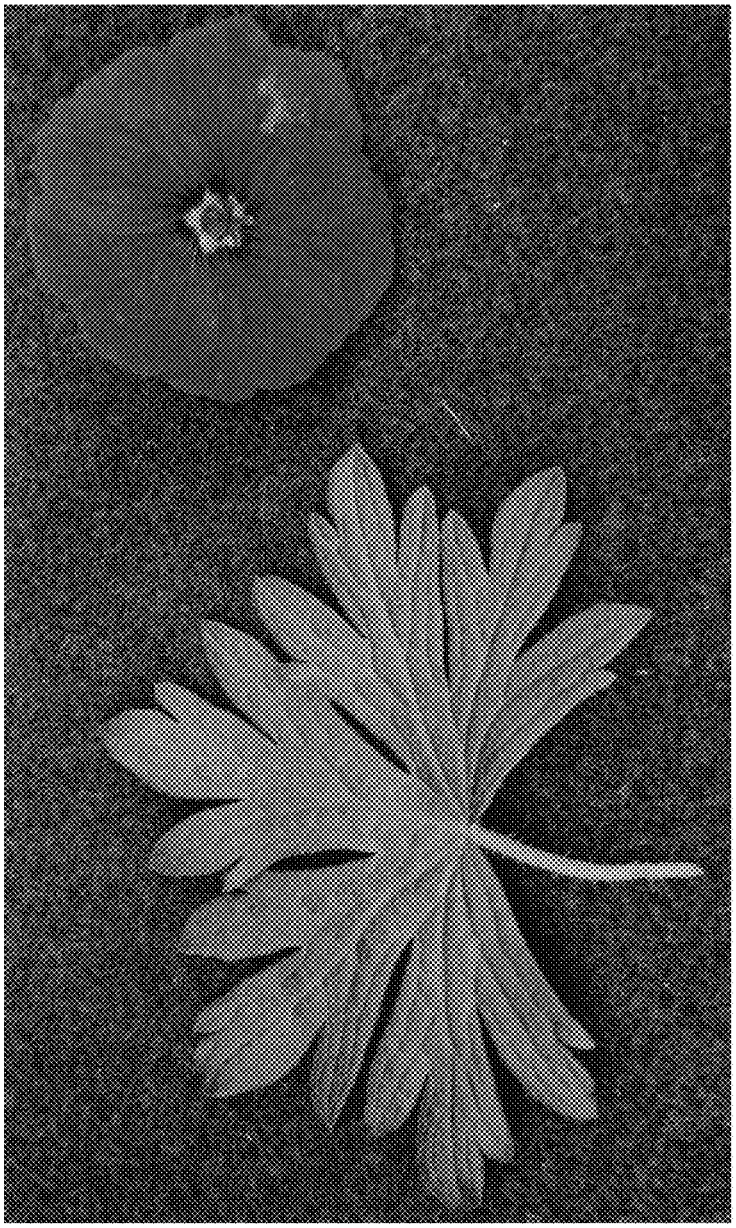

* * * * *